United States Patent

Henkin

[11] 4,051,847
[45] Oct. 4, 1977

[54] ANESTHESIA REBREATHING APPARATUS

[76] Inventor: Melvyn Lane Henkin, 19640 Greenbriar Drive, Tarzana, Calif. 91356

[21] Appl. No.: 622,382

[22] Filed: Oct. 24, 1975

Related U.S. Application Data

[62] Division of Ser. No. 448,816, March 7, 1974, Pat. No. 3,938,551, which is a division of Ser. No. 218,337, Jan. 17, 1972, Pat. No. 3,814,091.

[51] Int. Cl.² .......................................... A61M 16/00
[52] U.S. Cl. ................................. 128/145.6; 128/188
[58] Field of Search ............. 128/188, 186, 193, 194, 128/195, 145.8, 145.6, 145.5, 147

[56] References Cited

U.S. PATENT DOCUMENTS

| | | | |
|---|---|---|---|
| 2,902,269 | 9/1959 | Eichelman | 128/186 |
| 2,989,960 | 6/1961 | Hay | 128/188 |
| 3,033,195 | 5/1962 | Gilroy et al. | 128/145.8 |
| 3,077,191 | 2/1963 | Stanton | 128/188 |
| 3,721,239 | 3/1973 | Myers | 128/188 |
| 3,807,445 | 4/1974 | McPhee | 128/188 |
| 3,964,476 | 6/1976 | Palleni | 128/145.6 |
| 3,993,059 | 11/1976 | Sjostrand | 128/145.8 |

*Primary Examiner*—Robert W. Michell
*Assistant Examiner*—Henry J. Recla
*Attorney, Agent, or Firm*—Lindenberg, Freilich, Wasserman, Rosen & Fernandez

[57] ABSTRACT

A general anesthesia rebreathing system comprised of a disposable portion adapted to be easily coupled to and decoupled from a permanent portion. The disposable portion includes conventional breathing tubing for coupling a source of fresh gas, as from an anesthesia machine, to a patient and in addition an overflow tube for coupling the patient end of the system to an overflow (pop-off) valve, preferably mounted on the machine and constituting part of the permanent portion. The overflow tube entrance is located close to the patient end of the system and in communication with the tubing which conveys expired gas to a reservoir, such as a conventional breathing bag, mounted at the machine end. The arrangement assures that the patient's initially expired dead space gas is conveyed by the tubing to the reservoir with subsequently expired alveolar gas being exhausted through the overflow tube and pop-off valve. By preferentially exhausting alveolar gas in this manner, the need for using $CO_2$ absorber material within the system is minimized. For optimum performance, the pop-off valve is operable in two different modes, i.e. (1) as a manually controlled variable orifice and (2) as an automatically controlled valve responding to a positive control pressure. The source of control pressure is selectable by the attending anesthetist dependent on the type of ventilation being employed, i.e. spontaneous, manually assisted, or mechanically controlled.

2 Claims, 28 Drawing Figures

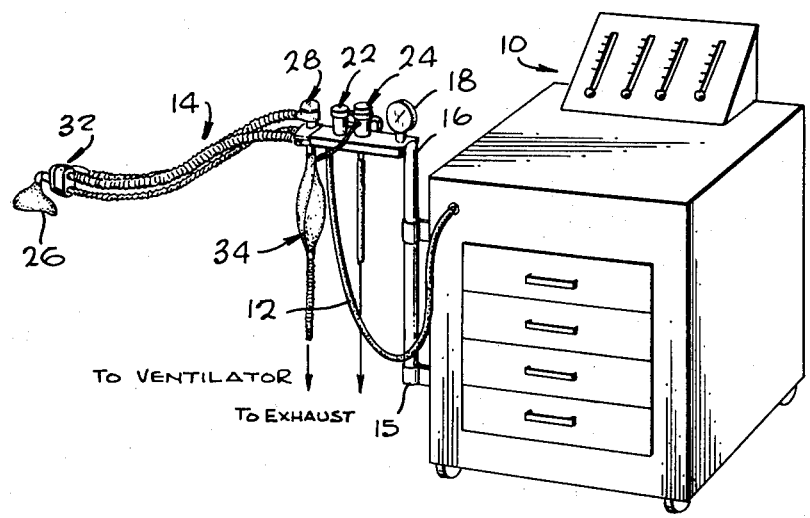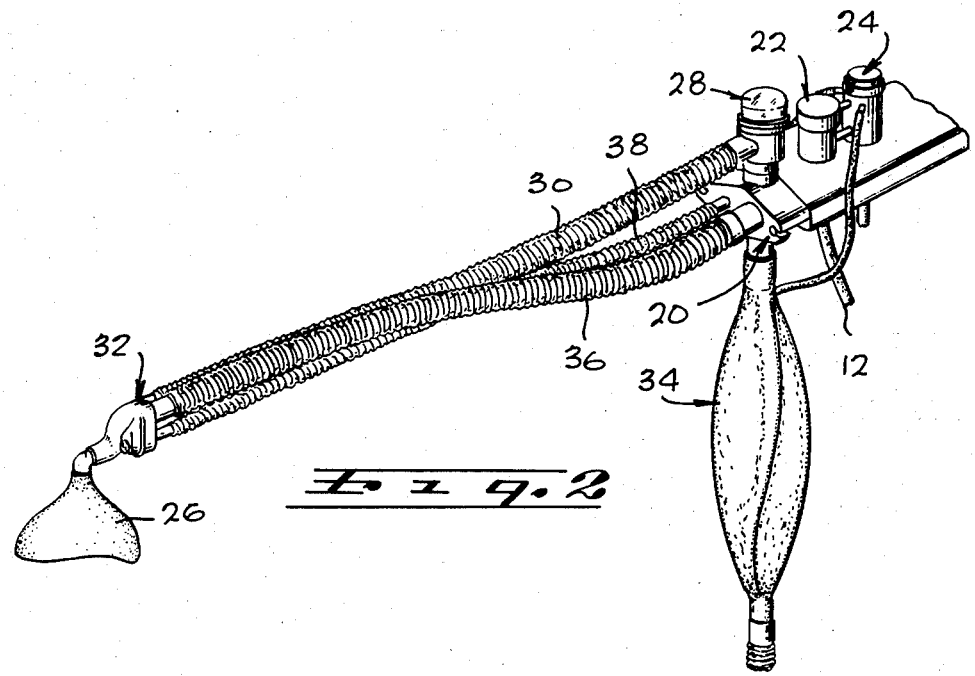

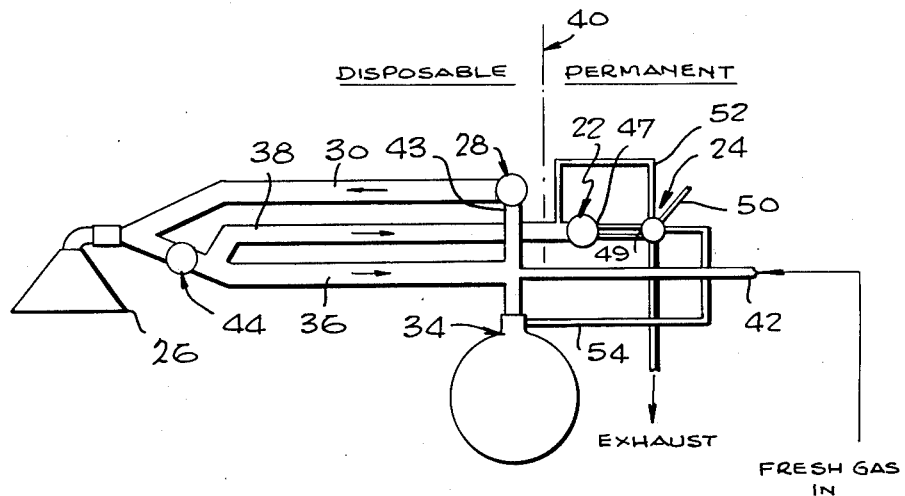
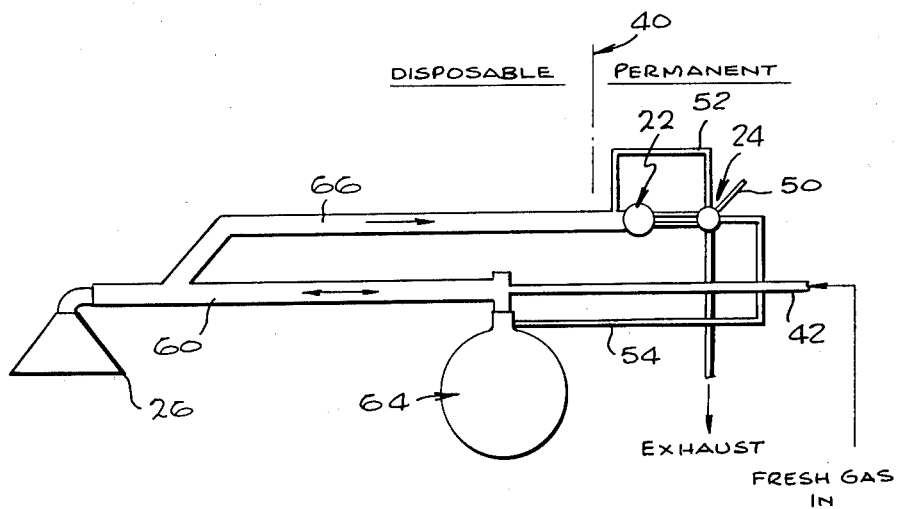

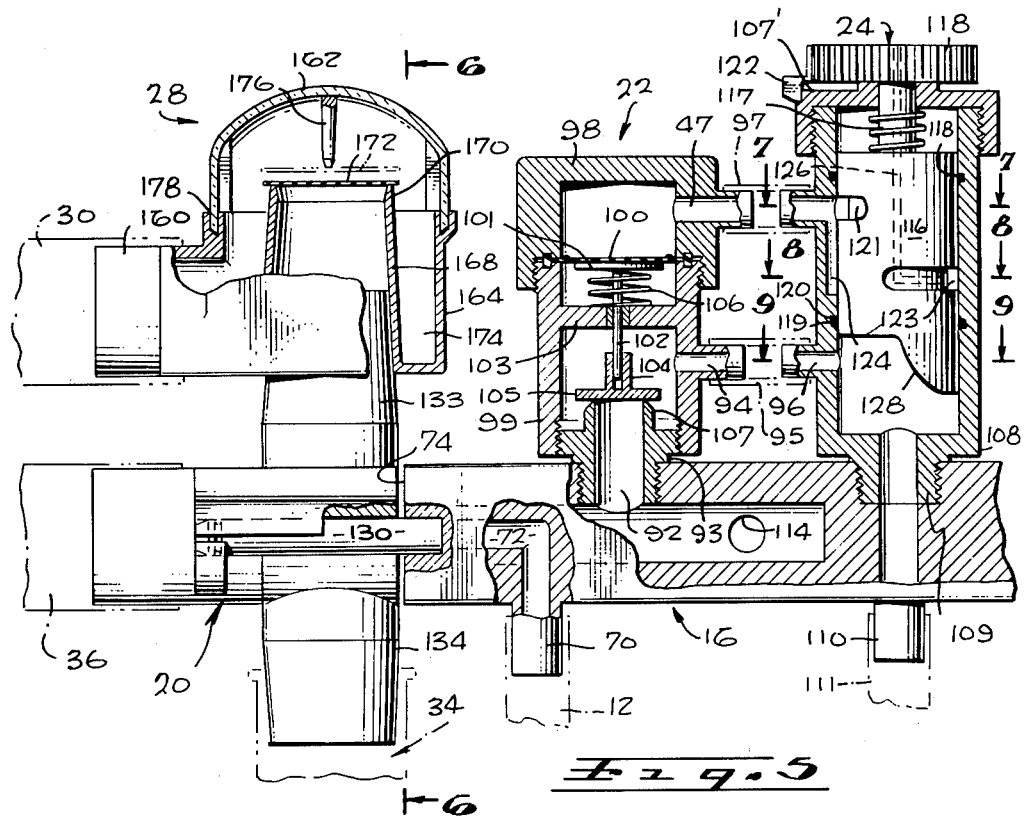
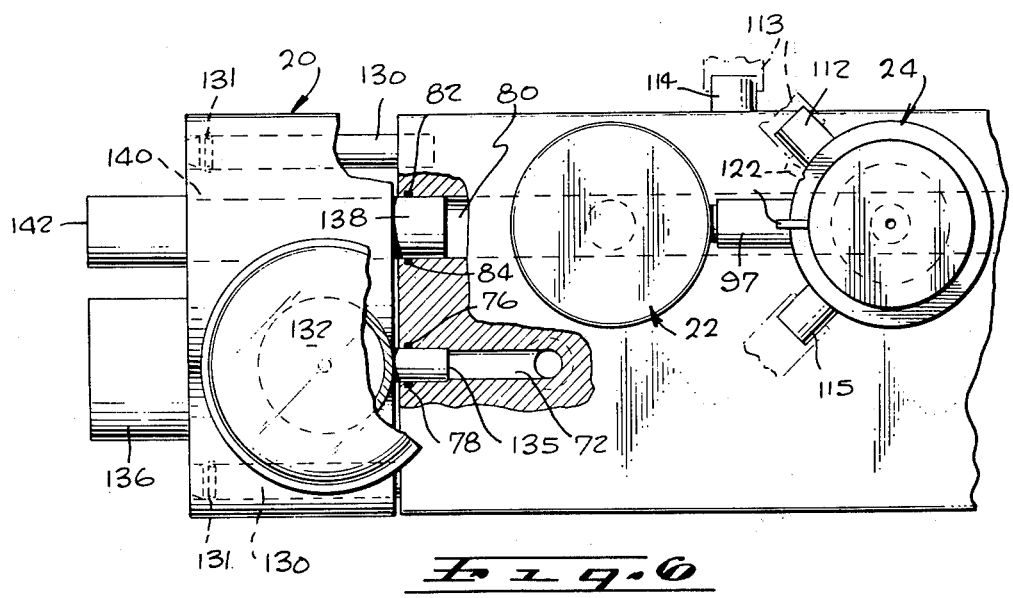

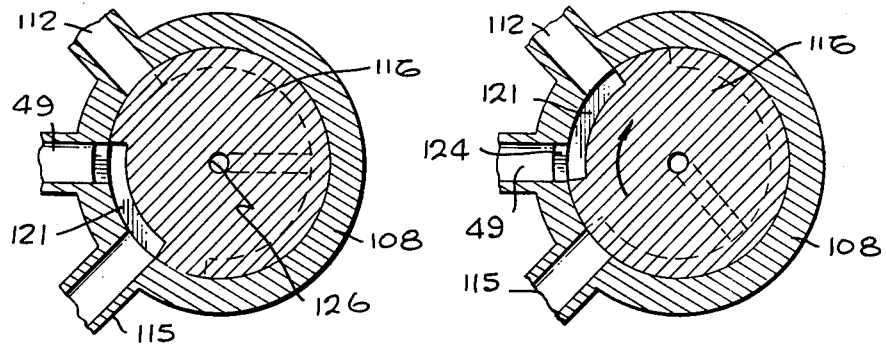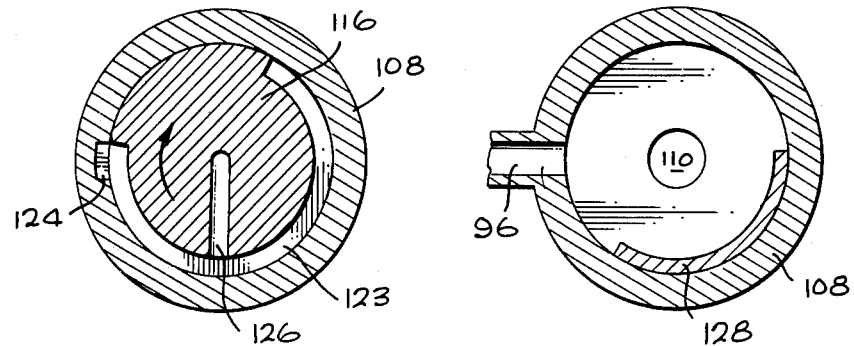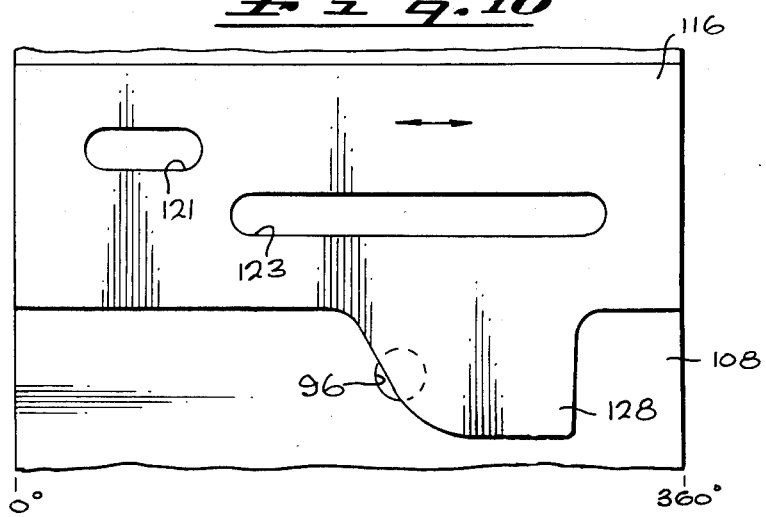

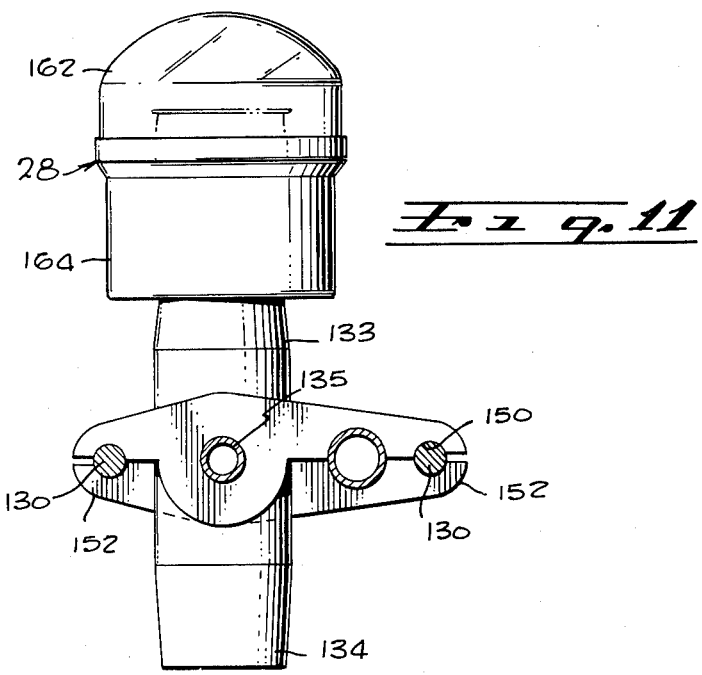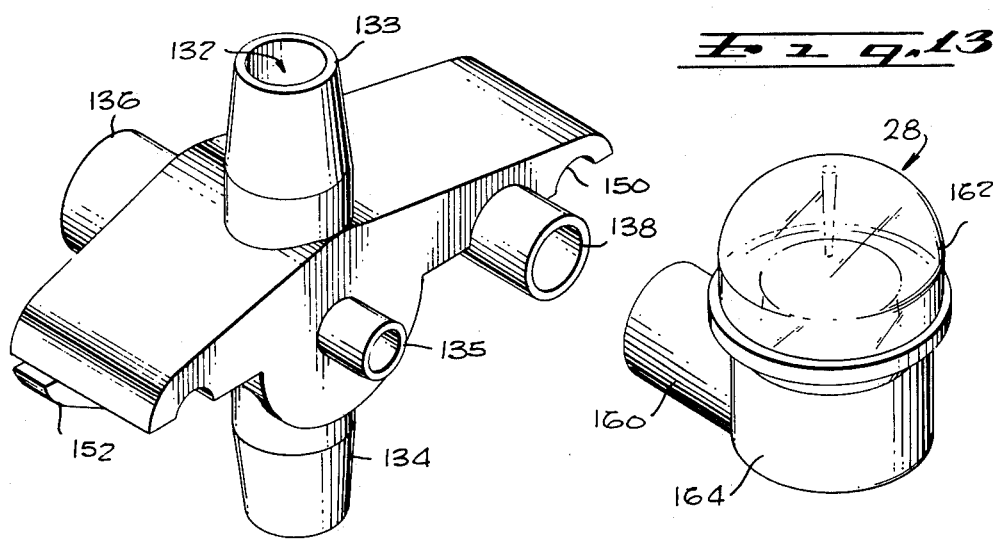

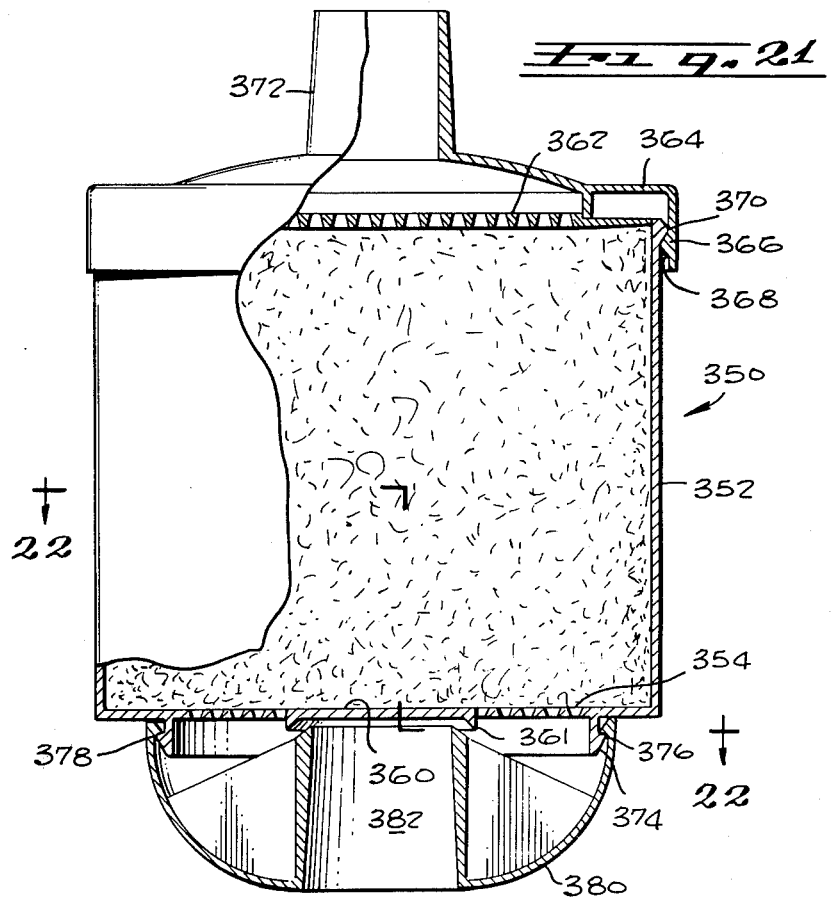
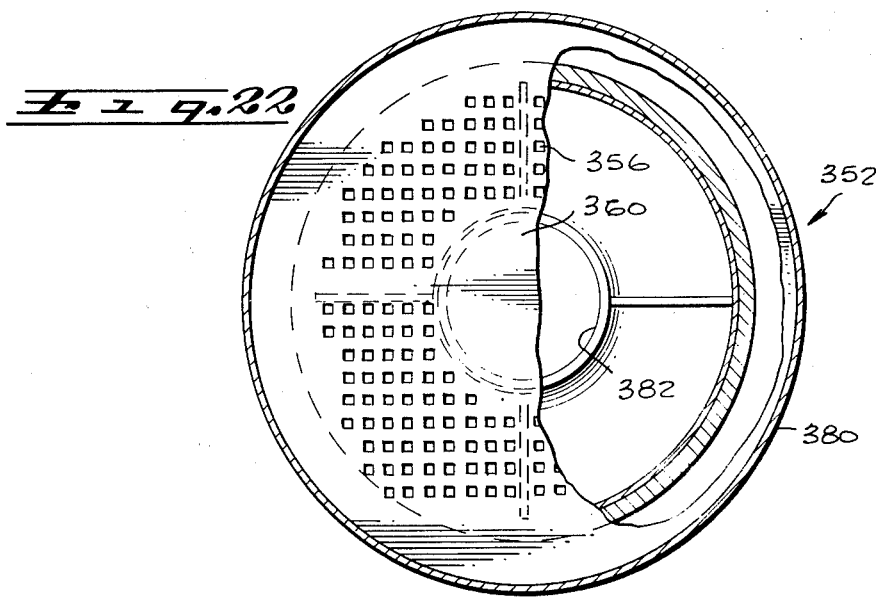

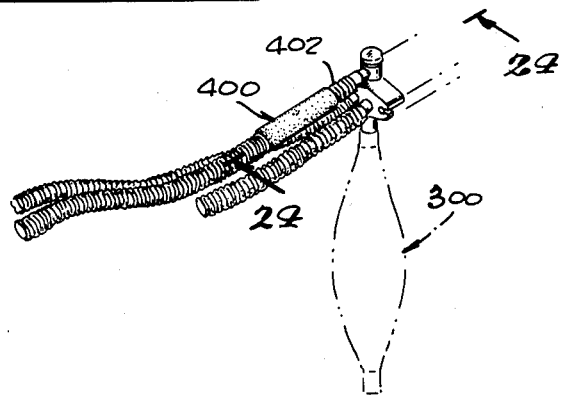
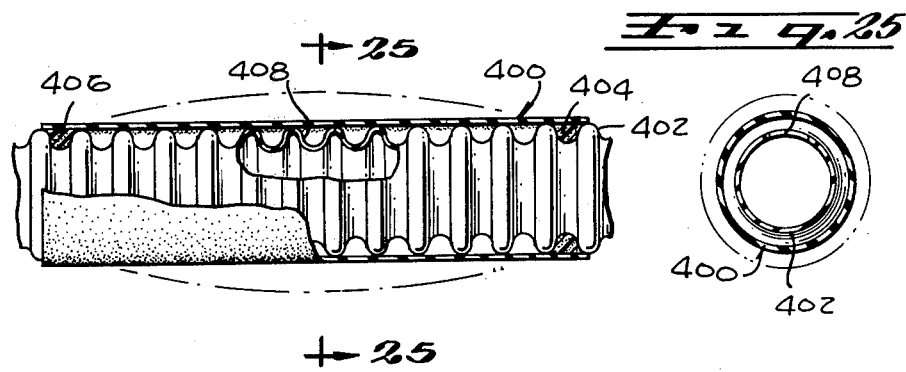
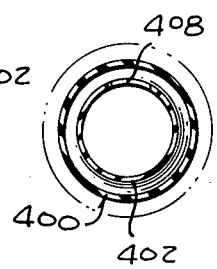
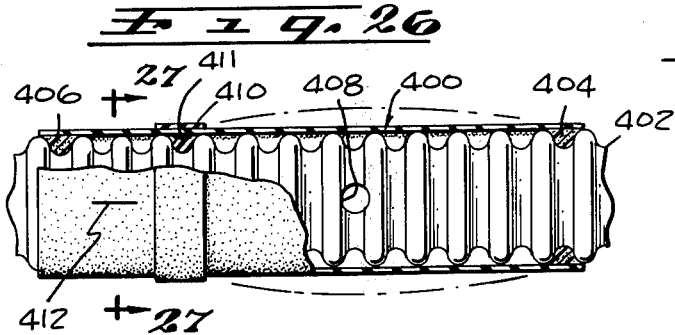
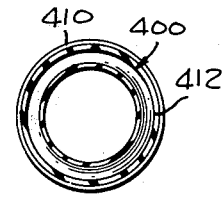

ANESTHESIA REBREATHING APPARATUS

BACKGROUND OF THE INVENTION

This is a division of application Ser. No. 448,816 filed Mar. 7, 1974 now Pat. No. 3,938,551, which in turn was a division of application Ser. No. 218,337 filed on Jan. 17, 1972, now Pat. No. 3,814,091.

This invention relates generally to apparatus for administering general anesthetics in the gaseous state and more particularly to an anesthesia rebreathing system, comprised of a permanent portion and a disposable portion.

The use of conventional general anesthesia administration apparatus inherently involves the danger of cross contamination between patients, sometimes with fatal results. Typically, such apparatus, for example an anesthesia circle, is comprised of one way valve controlled inspiratory and expiratory tubes communicating between an anesthesia machine providing fresh gases, and a patient. The inspiratory and expiratory tubes generally communicate with the patient's lungs via a tubular Y-piece and a mask or endotrachael tube. At the anesthesia machine end of the system, the expiratory tube normally communicates with the upper end of a canister of $CO_2$ absorber material. The lower end of the canister is coupled to the machine end of the inspiratory tube and to a gas reservoir such as a breathing bag. The fresh gas input from the anesthesia machine is usually coupled to the inspiratory tubbe close to the breathing bag. On expiration, the patient's gas is channeled through the one way valve in the expiratory tube to the $CO_2$ absorber material. On inspiration, the patient's gases are pulled through the inspiratory tube via the one way inspiratory valve, from the breathing bag and fresh gas supply. A pop-off valve is normally located proximate to the $CO_2$ absorber canister for exhausting expired gas.

It will, of course, be readily appreciated that in the utilization of such anesthesia apparatus, various parts of the apparatus are exposed to gas expired by the patient, who, if infected, will transmit bacteria throughout these parts. It has been found that cultures taken from such patient exposed parts will grow bacteria after the apparatus has been subjected to such cleaning procedures as are considered practical for each particular part of the apparatus.

In recognition of the foregoing contamination problem, recent attempts have been made to sufficiently reduce the cost of anesthesia apparatus so that most of the patient exposed parts can be discarded after a single use. Generally, these attempts have merely involved fabricating conventional apparatus in an inexpensive manner so that disposal is economically feasible. Such attempts have not, however, been too successful because cost reduction has not been sufficiently significant and because such cost reduction has necessitated the introduction of performance compromises which have often adversely affected the reliability and ease of use of various parts, such as the pop-off valve.

Accordingly, one of the important objects of the present invention is to provide an anesthesia rebreathing system comprised of a disposable portion and a permanent portion configured so as to minimize the structural complexity and cost of the disposable portion, while assuring that the disposable portion includes all elements which are likely to contaminate gas inhaled by a patient.

SUMMARY OF THE INVENTION

The present invention is directed to an improved general anesthesia administration system incorporating disposable circuit apparatus for coupling a permanent system portion to a patient. In accordance with a first embodiment of the invention, the circuit constitutes what is generally referred to as a circle, including both inspiratory and expiratory tubes. In accordance with a second embodiment of the invention, the circuit utilizes a single tube alternately used for inspiration and expiration. This second type of circuit is often referred to as a Magill type circuit. In accordance with the preferred embodiment of the invention, the permanent system portion is designed so that it can be used interchangeably with both circuit embodiment.

In accordance with an important aspect of the invention, both circuit embodiments incoroporate an overflow tube whose entrance communicates with the tubing carrying expired gas, close to the patient. The overflow tubbe exits at an overflow (pop-off) valve which can thus be located close to the anesthesia machine whereat it can be conveniently controlled by the attending anesthetist and can, preferably, constitute part of the permanent system portion. By locating the overflow tube entrance close to the patient, the overflow tube is able to function to preferentially vent alveolar gases, rich in $CO_2$, through the pop-off valve, and to save dead space and unbreathed gas, rich in $O_2$, within the tubing and reservoir for rebreathing. As a consequence, the maximum amount of $CO_2$ is vented, thus substantially eliminating the need to use $CO_2$ absorber material. The unidirectional flow in (away from patient) and the length (i.e. approximately three feed) of the overflow tube prevents the pop-off valve from contaminating gas inspired by the patient.

Both circuit embodiments incorporate a reservoir having flexible walls. Dead space gas initially expired by a patient is conveyed through the breathing tube to the reservoir with subsequently expired alveolar gas being conveyed through the overflow tube to the pop-off valve mechanism can be afforded while still minimizing the cost of the disposable circuit.

The reservoir wall is flexible so as to enable the patient's breathing to be assisted by squeezing the reservoir. Squeezing can be accomplished manually or with a mechanical ventilator. In accordance with a preferred embodiment of the invention, the reservoir is formed by a flexible outer wall having a flexible spetum mounted therein so as to define two isolated chambers. The first chamber is intended to communicate with a mechanical ventilator and the second chamber is intended to communicate with the circuit tubing. As the ventilator pressurizes the first chamber, the pressure is transmitted to the second chamber via the flexible septum and either the mechanical ventilator by the patient or the patient by the mechanical ventilator.

In accordance with a further feature of the invention, the pop-off valve is preferably selectably operable in two different modes; i.e., (1) as a variable orifice pressure elief valve or (2) as a balanced valve which closes in response to a positive control pressure, the mode being defined by the control pressure applied which can be selectively derived by the anesthetist from different sources dependent on the type of ventilation being employed; i.e., spontaneous, manually assisted, or mechanically controlled.

In accordance with a still further feature of the invention, a section of elastic material is preferably incorporated in the circuit tubing in communication with the pressure within the tubing. The elastic section stretches as pressure builds up within the circuit thereby preventing sudden step like increases in pressure which could be injurious to a patient's lungs. Use of the elastic section permits the use of inexpensive reservoirs having inelastic walls of plastic, for example, instead of requiring elastic wall, w.e., rubber, reservoirs which should otherwise be used to prevent sudden pressure increases.

In accordance with a still further aspect of the invention, an overpressure relief means is incorporated in the circuit, preferably close to the patient end, to maximize protection of the patient's lungs against accidental rupture due to overpressure malfunction in the rest of the system. In a first embodiment, an overpressure relief valve is formed within a housing common to the expiratory valve and Y-piece tubing coupling the mask or endotracheal tube to the breathing and overflow tubes. In a second embodiment, the previously mentioned elastic section is sealed to the breathing tube by an elastic band which stretches and leaks when the pressure within the breathing tube becomes excessive.

In accordance with a still further aspect of a preferred embodiment of the invention, an audible alarm means is incorporated in the overpressure relief means for alerting the anesthetist when an overpresssure condition exists.

Although, the need for using $CO_2$ absorber material is substantially eliminated in systems in accordance with the invention, in order to accommodate special circumstances and preferences of individual anesthetists, a $CO_2$ absorber canister is provided which can be used in the circle system at the option of the anesthetist. The canister is preferably constructed so as to be easily inserted in series with, and just upstream from the inspiratory valve.

BRIEF DESCRIPTION OF THE FIGURES

FIG. 1 is a perspective view of a general anesthesia rebreathing system embodiment in accordance with the present invention illustrating both the disposable and permanent portions system;

FIG. 2 is an enlarged perspective view better illustrating the disposable portion of the system of FIG. 1 and the interface between the disposable and permanent portions;

FIG. 3 is a schematic flow diagram of an anesthesia circle system in accordance with the invention;

FIG. 4 is a schematic flow diagram of a single tube (Magill type) anesthesia circuit system in accordance with the invention;

FIG. 5 is a side view, partially broken away, illustrating in detail the interface region of the system of FIG. 2 between the disposable and permanent portions;

FIG. 6 is a plan view, partially broken away, illustrating the interface region of the system shown in FIG. 5;

FIGS. 7A and 7B are sectional views taken substantially along the plane 7—7, of FIG. 5 respectively illustrating two different positions of the controller valve for coupling system pressure and ventilator pressure to the pop-off valve control port;

FIG. FIG. 8 is a sectional view taken substantially along the plane 8—8 of FIG. 5 illustrating a third position of the controller valve;

FIG. 9 is a sectional view taken substantially along the plane 9—9 of FIG. 5 illustrating the valve element in the controller valve for varying the pop-off valve exhaust orifice;

FIG. 10 is a developed view illustrating the relationship between the controller valve spool element and the pop-off valve exhaust orifice;

FIG. 11 is a side elevational view illustrating both the inspiratory valve structure and mounting unit for coupling the disposable anesthesia circuit to the system permanent portion;

FIG. 12 is a perspective view of the mounting unit shown in FIG. 11;

FIG. 13 is a perspective view of the inspiratory valve structure shown in FIG. 11;

FIG. 21 is an enlarged vertical sectional view taken through the $CO_2$ absorber canister of FIG. 20;

FIG. 22 is a horizontal sectional view taken substantially along the plane 22—22 of FIG. 21;

FIG. 23 is a perspective view similar to FIG. 2 except, however, illustrating the utilization of an elastic section for the purpose of preventing sudden pressure increases within the system;

FIG. 24 is a sectional view taken substantially along the plane 24—24 of FIG. 23;

FIG. 25 is a sectional view taken substantially along the plane 25—25 of FIG. 24;

FIG. 26 is a vertical sectional view similar to FIG. 24 illustrating a modified form of elastic section which functions to provide overpressure relief;

FIG. 27 is a sectional view taken substantially along the plane 27—27 of FIG. 26.

DESCRIPTION OF THE PREFERRED EMBODIMENTS

Figure 14:
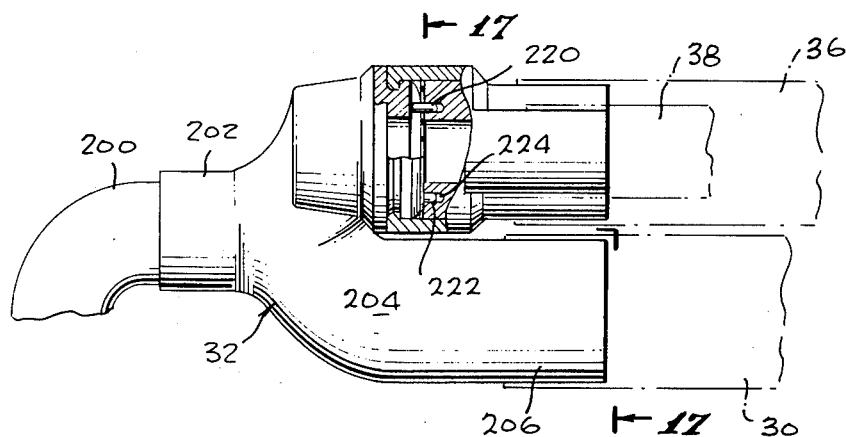
FIG. 14 is a side elevational view partially broken away illustrating the patient end of the circuit and more prticularly a preferred Y-piece embodiment containing the expiratory valve and overpressure relief valve.

Attention is now called to FIG. 1 which illustrates a general anesthesia rebreathing system in accordance with the present invention. Briefly, the rebreathing system as shown in FIG. 1 includes a substantially conventional anesthesia machine 10 which enables the attending anesthetist to meter and mix appropriate anesthetic agents which are then delivered to a supply hose 12 at an appropriate pressure, up to 50 psig. The gases supplied through hose 12 are then delivered through, what is generally referred to as an anesthesia circuit 14, to the patient. The anesthesia circuit 14 functions to:

1. Carry the gases to the patient and communicate with the patient's airway via a mask or endotrachael tube:

2. Serve as a reservoir between the varying flow in and out of the patient and the constant rate of supply;

3. Eliminate excess gas from the system;

4. Reduce the inspired concentration of $CO_2$ to acceptable levels; and

5. Enable the patient's breathing to be assisted or controlled by manual or mechanical means.

The machine 10 is normally provided with sleeves 15 for holding a mounting arm 16 which functions as a support for the anesthesia circuit and pressure gauge 18.

As has been previously pointed out herein, it is extremely difficult and impractical to fully sterilize all patient exposed parts of an anesthesia system after each use. As a consequence, it has long been recognized that utilization of anesthesia equipment presents a potential hazard of cross contamination between patients. In recognition of this potential hazard, efforts have been made in the prior art to fabricate the patient exposed parts sufficiently inexpensively to make disposal fter a single use economically feasible. These attempts thus far have been only moderately successful because the required cost reductions have compromised performance and reliability. The present invention is directed to an anesthesia system designed to minimize the complexity and cost of the disposable portion while retaining within the disposable portion all of the elements which are likely to contaminate patient inspired gas. Briefly, in accordance with the present invention, two embodiments of disposable anesthesia circuits are disclosed which can interchangeably be easily coupled to a common permanent system portion. The two anesthesia circuit embodiments represent modifications of circuits commonly known as (1) an anesthesia circle and (2) a single tube anesthesia circuit (Magill type). In accordance with the present invention, the permanent system portion is comprised of the machine 10 including up to the free end of the mounting arm 16. The disposable portion of the system mates easily via a quick disconnect coupling to the free end of the mounting arm 16.

More particularly, with continuing reference to FIG. 2, the circuit 14 is coupled to the mounting arm 15 by a mounting unit 20 which will be described in greater detail hereinafter. The mounting arm 16 has an overflow (commonly referred to as a "pop-off") valve 22 mounted near the free end thereof. As will be seen hereinafter, the operational mode of the valve 22 is selectable by the anesthetist by operation of a manual controller valve 24.

The mounting arm 16 and the elements fixed thereto, e.g. the pop-off valve 22 constitute part of the permanent or reusable portion of a system in accordance with the preferred embodiment of the invention. The circuit 14 constitutes the disposable portion and includes all of the hardware elements between the mounting unit 20 and the patient airway communication means, e.g., face mask 26. Briefly, the mounting unit 20 quickly connects and disconnects to the mounting arm 16 and provides gas flow paths therethrough to carry the gas supplied by hose 12 through the circuit 14 to the mask 26 and to carry $CO_2$ rich gases expired by the patient to the pop-off valve 22. The circuit illustrated in FIG. 2 constitutes an anesthesia circle and the flow path therethrough will be discussed in connection with FIG. 3. To facilitate identification of elements, it is pointed out that the circuit 14 of FIG. 2 includes an inspiratory valve 28 which passes fresh gas supplied from the hose 12 by the arm 16, through an inspiratory tube 30, to a Y-piece 32 coupled to the mask 26. Also in communication with the inlet side of the inspiratory valve 28 is a gas reservoir or breathing bag 34.

The Y-piece 32 is also coupled to the inlet end of an expiratory tube 36 which has an expiratory valve in series therewith (not shown in FIG. 2). The outlet end of the expiratory tube 36 is coupled to the mounting unit 20 and communicates with the inlet side of the reservoir 34.

As will be better appreciated hereinafter, in accordance with a significant aspect of the invention, the circuit includes an overflow tube 38 extending from the Y-piece 32 back to the mounting unit 20 where at it is in turn coupled to the input port of the pop-off valve 22.

Attention is now called to FIGS. 3 and 4 which respectively constitute schematic flow diagrams of two circuit embodiments in accordance with the present invention; namely (1) an anesthesia circle (FIG. 3) and (2) a single tube Magill type circuit (FIG. 4). Prior to considering the gas flow paths through these two circuits, it is important to recognize that the gas exhaled by a patient can appropriately be considered to consist of dead space gas and alveolar gas. The dead space gas enters only the mouth, nose, and large passages in the lungs and does not interact with the blood flowing through the lungs. Therefore, dead space gas leaves the patient as it enters except for changes in temperature and humidity. It gives up no oxygen ($O_2$) or anesthetic agent and takes up no carbon dioxide ($CO_2$).

On the other hand, alveolar gas does interact with the blood of the lung and it leaves the patient depleted in $O_2$ and rich in $CO_2$. In an adult having a tidal volume of 500 cc, 150 cc is normally dead space gas and 350 cc is normally alveolar gas. The circuits for FIGS. 3 and 4 in accordance with the present invention are configured so as to retain the dead space and unbreathed gases within the system and preferentially vent the $CO_2$ rich alveolar gases through the pop-off valve 22. Thus, with a fresh gas inflow above 4 liters per minute, the inspired $CO_2$ concentration remains acceptably low without requiring the use of $CO_2$ absorber material within the system.

Attention is now specifically called to FIG. 3 which depicts the flow paths through an anesthesia circle circuit embodiment in accordance with the present invention. Dashed line 40 in FIG. 3 represents the interface between the disposable portion to the left and the permanent portion to the right. Fresh gas is supplied through tube 42 shown in FIG. 3 to the inlet side 43 of inspiratory valve 28. The fresh gas enters via a small orifice (not shown) with a high pressure drop across it thus preventing any flow to and contamination from the permanent portion by the patient's expired gas. The inlet side of inspiratory valve 28 also communicates with the reservoir 34. The inspiratory valve permits gas flow therethrough only in the direction indicated by the arrow shown at the outlet side thereof, thus allowing gas to be inspired by a patient from the inspiratory tube 30. Gas expired by the patient is applied to the inlet side of expiratory valve 44. The outlet side of expiratory valve 44 communicates with the previous mentioned overflow tube 38 and expiratory tube 36. The other end of expiatory tube 36 communicates at the anesthesia machine end of the system with the reservoir 34. The machine end of the overflow tube 38 communicates with the pop-off valve 22 constituting part of the system permanent portion.

In the operation of the anesthesia circle of FIG. 3, fresh gas flows into the circle via tube 42 and the inspiratory and expiratory valves 28 and 44 keep the flow around the circle unidirectional. When the patient breathes in or the reservoir 34 is squeezed, the inspiratory valve 28 opens, the expiratory valve 44 closes, and fresh gas and gas from the reservoir 34 and inspiratory breathing tube 30 flow into the patient's airway via mask 26. When the patient breathes out, either spontaneously or because the pressure on the reservoir has been relaxed, the expiratory valve 44 opens and the inspiratory valvve 28 closes and gas flows from the patient to the expiratory breathing tube 36 into the reservoir 34. At the same time, fresh gas enters via the fresh gas inlet 42 and flows primarily into the reservoir.

At some point during expiration during spontaneous ventilation, the reservoir 34 becomes full and the gas near the patient end of the circuit starts flowing through the overflow tube 38 and out the pop-off valve 22, which during spontaneous ventilation, merely functions as a variable orifice pressure relief valve with an opening pressure of 1 cm of $H_2O$. This gas which is the last to leave the patient is alveolar gas which is rich in $CO_2$. The dead space gas, exhaled by the patient prior to expiration of the alveolar gas, is either further up the expiratory tube or in the distensible reservoir when the alveolar gas is exhaled.

Operation during manually assisted ventilation, i.e. when squeezing the reservoir, is similar to operation during spontaneous ventilation. However, flow out of the overflow tube 38 occurs during inspiration, i.e. when the reservoir is being squeezed, due to the pressure in the system. An alternative and preferred method of operation during manually assisted and controlled ventilation is to automatically positively close the pop-off valve 22 during inspiration when the reservoir is squeezed and permit it to open during expiration. As will be seen hereinafter when the operation of the pop-off valve is explained in connection with FIG. 5, an opertional mode for the pop-off valve can be selected by the anesthetist such that when system pressure increases in response to the reservoir being squeezed, the pop-off valve 22 is sealed closed. Relaxation of the pressure on the reservoir 34 reduces the pressure within the circuit so that on expiration by the patient, the dead space gas will initially flow through the expiratory tube and into the reservvoir 34 with the subsequently expired alveolar gas then flowing through the overflow tube 38 out the pop-off valve 22.

Thus, in summary, during spontaneous ventilation, the pop-off valve preferably comprises merely a variable orifice pressure relief valve which opens in response to pressure within the system. During manually assisted or controlled ventilation, the pop-off valve preferably seals closed in response to pressure within the system, i.e. insiration.

As will be seen hereinfter, the operational mode of the pop-off valve 22 is determined by the pressure applied to a control port 47 thereof. This control pressure is selected by the anesthetist by manual control of a three way controller valve 24. The valve 24 enables any one of three control pressures to be available at an output port 49 for application to the pop-off valve control port 47 for determining the pop-off valve operational mode. Briefly, the control input port 47 of the pop-off valve 22 can be exposed to ambient pressure via valve 24 and tube 50. In this position of the three way valve, the pop-off valve 22 will function merely as a variable orifice pressure relief valve. During manually assisted or controlled ventilation, in order that the pop-off valve seals closed during inspiration, the valve 48 is positioned so as to couple tube 52 to the pop-off valve control port 47 to apply system pressure thereto. When using a mechanical ventilator, and the preferred reservoir embodiment, to be discussed hereinafter in connection with FIGS. 18–20, the pressure provided by the ventilator can be coupled through tube 54 and valve 24 to the pop-off valve control port 47 to again assure that the pop-off valve 22 is closed when the system is being pressurized during inspiration.

Attention is now called to FIG. 4 which represents a schematic flow diagram of a single tube anesthesia circuit often referred to as a Magill type circuit. A Magill type circuit is characterized by the utilization of a single breathing tube 60 in lieu of the inspiratory and expiratory breathing tubes 30 and 36 of a circle system as shown in FIG. 3. Thus, gas flow through the breathing tube 60 of FIG. 4 is alternately toward the patient on inspiration and away from the patient on expiration. The Magill type circuit of FIG. 4 does not require the utilization of the unidirectional inspiratory and expiratory valves as is characteristic of the circle system of FIG. 3.

During spontaneous ventilation, using the system of FIG. 4, as the patient breathes in, he draws fresh gas from the inlet tube 60 and the reservoir 64. On expiration, his initially expired gas, constituting the dead space gas, will flow back through the breathing tube 60 to the reservoir 64. As the reservoir 64 becomes full, the subsequently expired alveolar gases will flow via the overflow tube 65 to the permanent pop-off valve 22. As has been previously pointed out, the permanent system portion can be used interchangeably with both the circle and single tube circuits of FIGS. 3 and 4.

During spontaneous ventilation utilizing the circuit of FIG. 4, the previously discussed pop-off valve 22 is operated in a variable orifice pressure relief mode by applying ambient pressure from tube 50 via three way valve 24 to the control port 47 of the pop-off valve. When ventilation is assisted or controlled by squeezing the reservoir 64, it is necessary to operate the pop-off valve 22 so that it seals closed in response to a pressure increase during inspiration or otherwise $CO_2$ rich gas will be retained within the system and fresh gas will exit through the pop-off valve. This operational mode is selected by applying either system pressure from tube 52, via valve 24, to the pop-off valve control part 47 or by applying ventilator pressure via tube 54 and valve 24 to the control port 47.

Attention is now called to FIGS. 5 and 6 which illustrate the structural details of the free end of the mounting arm 16 and the mounting unit circuit portion 20 which couples to the arm 16.

The mounting arm 16 is provided with a nipple 70 extending from the underside thereof for coupling to the previously mentioned fresh gas supply hose 12. The nipple 70 communicates with a fresh gas passgeway 72 extending parallel to the elongation of the arm 16. The passageway 72 opens at a front face 74 of the arm 16. An angular recess 76 is formed in the passgeway 72 near face 74 and retains an O-ring 78 therein for sealing around a male tube member of the mounting unit 20 adapted to project into the passgeway 72.

In addition to the passageway 72, the mounting arm 16 includes a passageway 80 which also opens at the front face 74 of the arm 16. An annular recess 82 is formed in passageway 80 near face 74 and it too retains an O-ring 84 for sealing around a male tube member of mounting unit 20, to be discussed hereinafter.

As was indicated with reference to FIGS. 4 and 5, the three way controller valve 24 functions to control the operational mode of the pop-off valve 22. The controller valve 24 is manually operable to selectively communicate any one of the three previously mentioned control sources to a control port of pop-off valve 22. In a first position, ambient pressure is applied to the control port, in a second position circuit pressure is applied to the control port and in a third position, ventilator pressure is applied to the control port. As will be seen, means are provided for automatically assuring that the pop-off valvve output orifice is fully open when either circuit or ventilator pressure is applied to the control port, corresponding to the operational modes used during manually assisted and controlled ventilation. On the other hand, when applying ambient pressure to the control port primarily used during spontaneous ventilation, means for varying the size of the pop-off valve output orifice are automatically moved into appropriate position.

With continuing reference to FIGS. 5 and 6, the pop-off valve 22 includes an input port 92 extending through externally threaded nipple 93, an output port 94, and the previously mentioned control port 47. The nipple 93 is threaded into the arm 16 and communictes the input port 92 with the circuit pressure in passageway 80. The output port 94 is coupled by a short tube 95 to an exhaust input port 96 in the housing of controller valve 24. The control port 47 is coupled by a short tube 97 to previously mentioned port 49 of the controller valve 24.

The pop-off valve 22 includes a housing comprised of upper portion 98 threaded into lower portion 99 which in turn is threaded into nipple 93. A flexible diaphragm 100 is held around its circumference between opposed surfaces of housing portions 98 and 99. Disc 101, bearing against the underside of the diaphragm, has a rod 102 depending therefrom. The rod 102 extends through, in sealed relationship, a fixed wall 103 and into a recess defined in boss 104 formed in valve leaf 105. A coil spring 106 is contained around rod 102 between wall 103 and disc 101.

In the operation of the pop-off valve 22, when ambient pressure is available on the upper surface of diaphragm 100, the spring 106, will force the rod 102 to the position shown in FIG. 5, in which its end is spaced from the bottom of the recess in boss 104 of valve leaf 105. As a consequence, valve leaf 105 which normally rests on and seals against knife edge 107 on nipple 93 will be lifted when the pressure within passageway 80 exceeds a first threshold, e.g., 1 cm of H$_2$O, to permit gas flow from passageway 80 out through port 94.

On the other hand, when a positive pressure is applied to the upper surface of diaphragm 100 (from the circuit or ventilator via the controller valve 24, as will be discussed hereinafter), the diaphragm 100 will be bowed downwardly to bottom rod 102 in the recess in boss 104 thereby positively sealing valve leaf 105 against knife edge 107. It is pointed out that the active area of diaphragm 100 is greater than the active area of valve leaf 105 and as a consequence, the valve leaf 105 will be sealed closed when equal pressures are applied through the control port 47 and input port 92 and the pressure on the diaphragm exceeds a second threshold, e.g., 5 cm of H$_2$O.

The controller valve 24 functions to enable an anesthetist to selectively apply either ambient pressure, circiut pressure or ventilator pressure to the control port 47 for operating the pop-off valve in the aforedescribed manner. As will be seen, when ambient pressure is applied, the controller valve 24 also enables the anesthetist to vary the size and thus the flow rate out of the pop-off valve output port 94. When circuit pressure or ventilator pressure is applied, the output port 94 is left fully open.

The controller valve 24 comprises a spool valve having a housing comprised of an upper portion 107' threaded onto a lower portion 108. Lower portion 108 has an externally threaded nipple 109 threaded into arm 16. Nipple 109 has a central bore therethrough which communicates the exhaust input port 96 through arm 16 to nipple 110. A system exhaust hose 111 is intended to be coupled into nipple 110 for carrying exhausted gas away, preferably out of the operating room, to prevent any adverse effect upon the personnel present.

From what has previously been said, it should be recognized that three different pressure sources (including ambient) are applied to the input side of controller valve 24 for selective coupling by the anesthetist to the port 49 for communication through tube 97 to the pop-off valve control port 47. One of these three sources comprises circuit pressure (corresponding to tube 52 in FIG. 3) which is available through nipple 112 via a hose 113 from nipple 114 in communication with passageway 80 through arm 16. A second of the sources is derived from ventilator pressure (corresponding to tube 54 in FIG. 3) through nipple 115 and will be discussed in greater detail in connection with the description of FIGS. 18–20.

Communication from either nipple 112 or nipple 115 to port 49 is controlled by the position of a spool 116 mounted for rotation within lower housing portion 108. Spool 116 has a shaft 117 coupled thereto which in turn is connected to a knob 118 available for manual rotation by the anesthetist. The inner surface of housing portion 106 is provided with annular recesses 118 and 119 each of which retains an O-ring 120. Spool 116 is provided with a slot 121 extending around a portion of the circumference thereof of sufficient length to bridge the distance between nipples 112 and 115 and port 49. More particularly, with the spool rotated to the position of FIG. 7A, slot 121 will communicate nipple 115 with port 49. When spool 116 is rotated to the position of FIG. 7B, slot 121 communicates nipple 112 with port 49. In order to facilitate the anesthetists positioning of the spool, the knob 118 is preferably provided with a pointer 122 which can be appropriately detented in two position.

In order to selectively communicate a third pressure source, i.e., ambient (corresponding to tubbe 50 of FIG. 3) with port 49 the spool 116 is provided with an additional slot 123 extending greater than 180° around the circumference thereof. The slot 123 is vertically displaced from the slot 121 but is still able to communicate with port 49 (see FIG. 8) as a consequence of the provision of vertical slot 124 in communication with port 49. Slot 123 communicates with ambient pressure via passageway 126 through the spool 116, shaft 117 and knob 118. Inasmuch as it is necessary to prevent communication between slots 121 and 123, the spool circumferential surface and the lower housing portion inner surface are correspondingly tapered and a spring 127 is provided around shaft 117 to seat the spool in the tapered housing so that the housing inner surface seals the slots.

As previously pointed out, it is desirable to enable the anesthetist to variably control the flow out of the pop-off valve exhaust port 94 when the pop-off valve is being operated in the pressure relief mode to assure the maintenance of an adequate gas supply within the circuit. On the other hand, when the pop-off valve is being operated in the balanced mode it is desirable that the pop-off valve exhaust be wide open. In order to accomplish this, the spool is provided with a valve member 128 depending from the lower end thereof and shaped so as to variably cover the port 96 as the knob 118 and spool 116 are rotated. The variable covering of the port 96 can best be seen in the developed view of FIG. 10 which shows how the valve member 128 wipes across the port 95. Note that the valve covers the port 96 only when slot 123 communicates with port 49 and is remote from and has no effect on the port 96 when the slot 121 is in communication with port 43.

The front face 74 arm of the mounting arm 16 is provided with a pair of forwardly projecting pins 130 each of which has an annular groove 131 formed therein at the forward end thereof. These pins 130 are utilized to align and retain the mounting unit 20 relative to the arm 16 so as to provide mechanical support and gas flow communication therebetween.

Attention is now called to FIGS. 11 and 12 which better illustrate the mounting unit 20. The mounting unit 20 comprises a structure defining internal passageways and terminating in male nipples adapted to communicate with female fittings on mating parts. More particularly, the unit 20 defines a large vertical bore 132 terminating in male nipples 133 and 134 which preferably comprise 22 millimeter outer diameter tapered fittings. The nipple 134 is intended to be received in the upper opening of the reservoir 34 as represented in FIGS. 5 and 7. The nipple 133 is intended to project into a correspondingly tapered fitting defined within the housing of inspiratory valve 28 as is also represented in FIGS. 5 and 7. Also in communication with the large bore 132 is nipple 136 which is 22 millimeters in diameter. This fitting is intended to project into the expiration breathing tube 36 as is represented in FIGS. 2, 5 and 6. Nipple 135, which also opens into large bore 132 is adapted to project into and communicate with passageway 72, in arm 16, as shown in FIG. 6. The mounting unit 20 further includes a nipple 138 which is adapted to project into and communicate with the passageway 80 in the mounting arm 16. Nipple 138 communicates with a passageway 140 extending straight through the mounting unit 20 and terminating in a nipple 142 intended to be coupled into overflow tube 38 as represented in FIGS. 2 and 6.

The mounting unit 20 is provided with a pair of parallel channels 150 extending along the underside thereof as shown in FIG. 12. A resilient finger 152 is formed in the mounting unit 20 immediately adjacent the channel 150 for locking into the annular groove 131 formed on the pins 130 of mounting arm 16. That is, in order to couple the disposable anesthesia circuit to the permanent mounting arm 16, the channels 150 of the mounting unit 20 are placed on the pins 130 and then the mounting unit 20 is pushed toward the front face 74 of the mounting arm 16 until the resilient fingers 152 of the mounting unit 20 lock into the annular grooves 131 on the pins 130. This action positions the nipples 135 and 138 of the mounting unit 20 in the passgeways 72 and 80 of the mounting arm 16 with seals being achieved by O-rings 78 and 84.

Still referring to FIG. 5, the inspiratory valve 28 is a unidirectional valve which permits gas flow upwards from the nipple 133 on mounting unit 20 through the inspiratory valve 28 and out through the exhaust port within nipple 160. Inspiratory valve nipple 160 is also preferably a 22 millimeter diameter fitting adapted to receive the inspiratory tube 30 thereon as represented in FIGS. 2 and 5.

The inspiratory valve 28 is comprised of a two piece housing including a cover 162 and a lower portion 164. The lower portion 164 is provided with a cylindrical tapered wall 168 defining a central opening into which the male nipple 133 is force fit as shown in FIG. 5. A knife-edge 170 is formed on the upper edge of wall 168 for co-operation with a valve leaf 172. A trough 174 formed around wall 168 communicates with the exhaust port defined within tapered nipple 160. In the operation of the inspiratory valve 28, in response to a positivve pressure differential from the lower to the upper side of valve leaf 172, as seen in FIG. 5, the valve leaf 172 will be lifted so as to provide communication between the bore 132 of the mounting unit 20 and the exhaust port defined within inspiratory valve nipple 160. The inspiratory valve cover 162 is provided with a depending in 176 which limits the movement of the valve leaf 172. The edges of the cover 162 are adapted to be received within an annular recess 178 formed in the lower portion of the inspiratory valve housing in sealed relationship.

From the foregoing, the interface between the disposable anesthesia circuit and the permanent portion at the machine end of the system should be appreciated. The configuration of the disposable mounting unit 20 is such that it can be easily and quickly connected and disconnected from the permanent system portion as the permanent portion is used with successive patients.

Attention is now called to FIGS. 14-17 which illustrate a preferred Y-piece embodiment 32 to be employed in a system in accordance with the present invention. The preferred Y-piece embodiment 32 functions to couple a mask elbow 200 or endotracheal tube adaptor to the breathing tubes 30 and 36 and overflow tube 38. As shown in FIG. 14, the mask elbow terminates in a 15 millimeter tapered fitting adapted to seat in sealed relationship within the bore 202 defined at the entrance to the Y-piece 32. The Y-piece 32 defines a curved passageway 204 terminating in a nipple 206 adapted to be secured to the patient end of the inspiratory tube 30. The upper portion of the Y-piece 32, as shown in FIG. 14, includes both the expiratory valve and an overpressure relief means.

Figure 15:
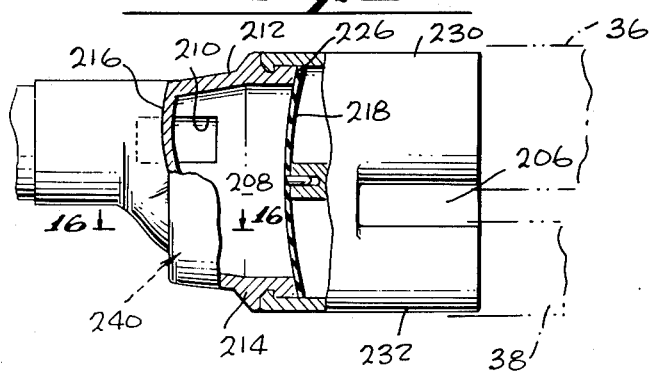
FIG. 15 is a sectional view taken substantially along the plane 15—15 of FIG. 14.

More particularly, the bore 202 of the Y-piece 32 communicates with a chamber 208 through passageway 210. Chamber 208 is defined by three solid walls 212, 214, and 216 and by a fourth wall constituting a valve leaf 218. the valve leaf 218 has two pins 220 and 222 secured thereto which are received and retained within pin wells 224 formed within the Y-piece housing. The face 226 of walls 212 and 214 is curved to define a valve seat surface. When the valve leaf 218 is in its quiescent state, as represented in FIG. 15, it is slightly stressed in bowed relationship about an axis through pins 220 and 222. As a consequence, the valve leaf 218 bears against and conforms to the valve seat surface 226. The valve leaf 218 of course prevents gas flow from right to left in FIG. 15 since pressure on the right side of valve leaf 218 merely better seats the valve leaf. On the other hand, in response to a positive pressure differential from the left to the right side of valve leaf 218, as seen in FIG. 15 the valve leaf 218 bends about the axis through pins 222 and 224 thereby permitting gas flow around the edges of the valve leaf. When the valve leaf 218 opens under pressure, it communicates the chamber 208 with male nipples 230 and 232. As represented in FIG. 15, nipple 230 is intended to fit into and seal with expiratory tube 36 and male nipple 232 is intended to fit into and seal with overflow tube 38.

Figure 16:
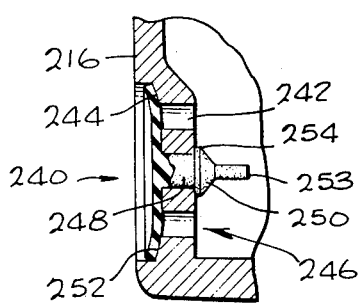
FIG. 16 is an enlarged sectional view taken substantially along the plane 16—16 of FIG. 15 illustrating the details of an overpressure relief valve.
Figure 17:
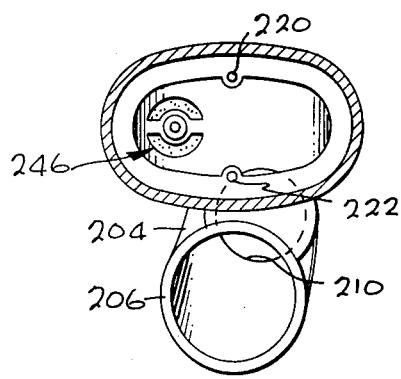
FIG. 17 is a sectional view taken substantially along the plane 17—17 or FIG. 14.

In accordance with a preferred embodiment of the invention, the Y-piece 32 additionally includes an overpressure relief means 240 which thereby is located close to the patient and thus provides maximum protection against lung rupture which could otherwise occur due to overpressure malfunction in the system. The overpressure relief means 240 communicates with member 208 and is comprised of a cup shaped recess 244 formed in the outer surface of wall 216 (FIG. 16). Apertures 242 extend through the wall 216 from the cup shaped recess 244 to the chmber 208. An elastic valve member 246 is provided which includes a central shaft portion 248 which extends through the wall 216 in the center of the cup shaped recess 244. A small flange 250 is formed on one end of the shaft 248 and a larger flange 252 is formed on the other end. A pull tab 253 extends axially from the small flange 250 remote from the shaft 248. The elastic valve member 246 is installed into the position shown in FIG. 16 by pulling the tab 253 to the right through the central opening in the cup portion 244. As a consequence of the external surface 254 on the flange 250 being tapered and as a consequence of the elastic qualities of the valve member, the flange 250 can be pulled through the central hole to arrive at the position illustrated in FIG. 16. In this position, the flange portion 252 will conform to the cup shape of the recess 244. When in the quiescent condition shown in FIG. 16, the shaft 248 of the valve member 246 will be under slight stress thereby pulling the valve flange 252 tightly against the recess 244 and sealing the apertures 242. However, as the pressure in chamber 208 increases, it will bear outwardly (toward the left in FIG. 16) against the valve flange 252. This action will distort the shape of the valve flange 252 and stretch the shaft 248 thereby permitting flow through the apertures 242 and relieving pressure from the chamber 208 and thus from the entire circuit. As gas escapes through apertures 242 past valve flange 252, it will produce an audible alarm as the flange 252 vibrates.

Figure 18:
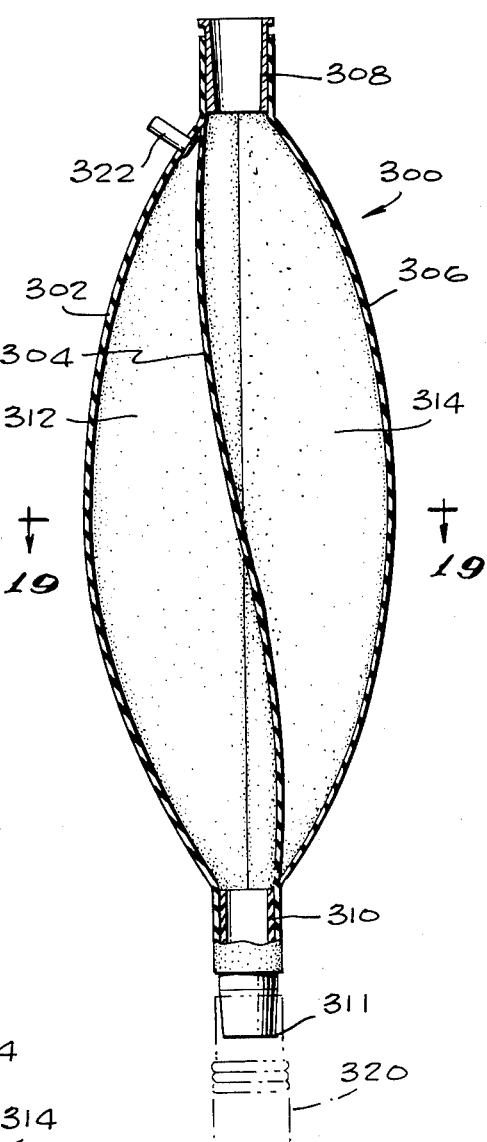
FIG. 18 is a sectional view of a preferred form of reservoir in accordance with the present invention for isolating a mechanical ventilator from a patient's gas.
Figure 19:
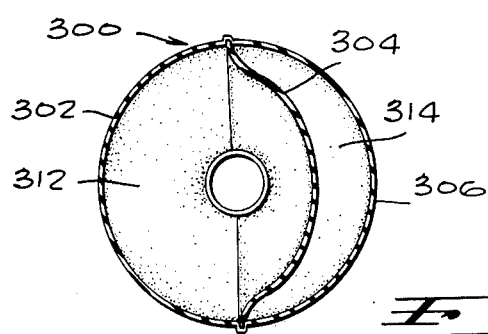
FIG. 19 is a sectional view taken substantially along the plane 19—19 of FIG. 18.

Attention is now called to FIGS. 18 and 19 which illustrate a preferred reservoir embodiment in accordance with the present invention. As has been previously mentioned herein, the reservoir thus far referred to, can constitute a conventional single compartment breathing bag. However, although such a bag might be adequate for spontaneous and manually assisted ventilation, it would not be satisfactory for controlled ventilation where the reservoir is squeezed by a mechanical ventilator since the ventilator would then be exposed to the patient's gas and would constitute an avenue for cross-contamination between patients.

Figure 20:
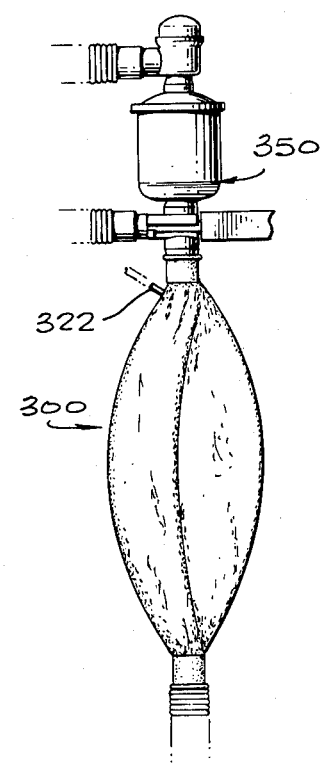
FIG. 20 is a side elevational view illustrating the manner in which the reservoir of FIGS. 18 and 19 is structurally incorporated in the system and further illustrating the incorporation of a canister of $CO_2$ absorber material between the reservoir and inspiratory valve.

Accordingly, a reservoir 300 is provided, as illustrated in FIGS. 18-20, which isolates the ventilator from the patient's gas. The reservoir 300 includes a pair of hermetically isolated chambers which respectively communicate with the anesthesia circuit and the ventilator. The reservoir 300 preferably is formed utilizing three layers of vinyl sheeting 302, 304 and 306 which are welded to each other and to fittings 308 and 310.

The fitting 310 communiates with a chamber 312 formed between sheets 302 and 304 and the fitting 308 communicates with a chamber 314 formed between the sheets 304 and 306. The fitting 308 is a 22 millimeter fitting adapted to force fit onto tapered male nipple 132 of the mounting unit 20 as represented in FIGS. 5 and 7. the fitting 310 is provided with a terminal taper 311 intended to be force fit into the end of a corrugated tube 320 which in turn is coupled to a mechanical ventilator (not shown).

In the use of the ventilator isolator reservoir 300 of FIGS. 18-20, the ventilator will periodically pressurize the chamber 312. The pressure on the isolating septum sheet 304 will be transmitted to the chamber 314 thereby producing a correlary pressure within the inspiratory breathing tube 30. The outer sheets 302, 304, 306 of the reservoir 300 of FIG. 18 and 19 should be thin, flexible and inelastic. The exterior contour of the reservoir 300 is preferably similar to the contour of conventional breathing bags so that the "feel" is similar. The septum sheet 304 is peferably contoured similar to sheets 302 and 306 so that it may sweep the entire volume of reservoir 300 with minimal pressure differential across the septum sheet. Preferably, the septum sheet 304 should be a visible color and at least one outer sheet should be transparent so that volume changes caused by movement of the septum sheet can be readily observed by the attending anesthetist. By providing the reservoir 300 with thin and flexible outer walls, it will function as a conventional breathing bag during manually assisted ventilation since it can be readily squeezed by the anesthetist and the conventional feel will only be minimally modified by the presence of the septum sheet 304.

It has previously been mentioned with respect to the operation of the pop-off valve 22 that is is preferable, under conditions of controlled ventilation, to make the pop-off valve responsive to ventilator pressure. That is, it will be recalled that when the system is pressurized by the ventilator during inspiration, it is desirable to close the pop-off valve. It will further be recalled that for this purpose, reference was made to a tube 54 in FIG. 2 coupled to the input side of the three way controller valve 24, i.e., to nipple 115 in FIG. 6. In order to communicate the ventilator pressure to the nipple 115, a nipple 322, in communication with chamber 312, is provided within sheet 302 of reservoir 300. One end of the tube 54 fits onto the nipple 322. Alternately, pressure may be supplied to tube 54 from a side port nipple on the tapered 22 millimeter male fitting 311 which connects corrugated tube 320 to the ventilator chamber 312 of the reservoir 300.

It has been previously pointed out that utilization of the overflow tube in the manner indicated to preferentially vent alveolar gases eliminates the need to use $CO_2$ absorber material under most circumstances. However, it has also been recognized that special circumstances (e.g., fresh gas inflow less than 4 liters per minute) or personal preferences of the anesthetist may dictate that $CO_2$ absorber material be used. In accordance with a preferred embodiment of the invention, a canister 350 (FIG. 20) is provided for optional incorporation between the tapered male nipple 133 of the mounting unit 20 and the tapered female opening in inspiratory valve 28.

Reference is now directed to FIGS. 21 and 22 which illustrate the details of the $CO_2$ absorber material canister 350. The canister 350 includes a cylindrical central portion 352 whose bottom wall 354 is perforated at 356 around an unperforated central portion 360. A fluid guide ring 361 is provided on the undersurface of wall 354 around the central portion 360. A perforated plate 362 fits over and covers the cylindrical container 352. The plate 362 is held in place by a cover 364 having a depending flange 366 which defines an inwardly projecting annular ring 368 adapted to lock against outwardly projecting annular ring 370 on the central portion 352. The cover 364 is provided with a tapered 22 millimeter male fitting 372, identical to the fitting 130 on the mounting unit 20, and consequently receivable in the female opening defined in the housing of the inspiratory valve 28.

An annular flange 374 is formed on the lower surface of the wall 354 as shown in FIG. 21. The outer surface of the flange 374 has an outwardly projecting annular rim 376 adapted to mate with and lock against an inwardly projecting annular rim 378 formed on a sump collector unit 380. The sump collector unit 380 is comprised of a housing defining a cylindrical female opening 382 for receiving the tapered male fitting 130 of the mounting unit 20. A trough 384 is formed around the fitting 382 and functions as a sump to collect caustic fluids generated during operation and to prevent accidental spillage or flow to the patient. As a consequence of making the central portion of wall 354 solid, and by providing the fluid guide ring 361, any caustic fluid generated will be directed into the sump and not into the breathing system.

Although utilization of systems in accordance with the teachings of the present invention to preferentially exhaust alveolar gas virtually eliminates the need to use $CO_2$ absorber material, it has been shown that such material can be easily incorporated into the system when desired. When $CO_2$ absorber material is employed, it is of course depleted at a very slow rate. It is further pointed out that where desired, as in situations of long duration surgery, two or more $CO_2$ canisters of the type shown in FIGS. 21 and 22 can be incorporated in series within the system between the mounting unit 20 and the inspiratory valve 28.

In order to minimize the cost of the disposable portion of the anesthesia system, it is preferable to construct the reservoir of plastic material rather than rubber. However, since plastics are inelastic, they permit rapid and excessive pressure build-up in the patient's airway. In recognition of this hazard, respected authorities have suggested that only rubber breathing bags be utilized. The advantage of using a rubber breathing bag, as contrasted with a bag of inelastic material, is that as the pressure in the breathing circuit increases, the rubber bag stretches and therefore the pressure increases less rapidly and there is more time for the anesthetist to recognize and abort the developing danger. Moreover, as a rubber bag increases in size, a maximum pressure is reached beyond which greater distention results in a decreasing pressure within the bag and by like reasoning within the patient's airway. Proper design of the bag volume, wall thickness, and material elasticity can assure that the peak pressure is within a safe range.

Although the foregoing advantages of rubber breathing bags are recognized, it has also been recognized that such bags are relatively difficult and expensive to fabricate. In view of this, attention is now called to FIGS. 23-25 which illustrates a construction which permits utilization of inelastic material breathing bags and yet which also retains the advantageous characteristics of rubber breathing bags.

More particularly, as shown in FIGS. 23-25, a section of elastic tubing 400 is mounted around one of the breathing tubes with the ends of the elastic tube secured and sealed to the breathing tube 402 at 404 and 406. An opening 408 is formed within the breathing tube 402 in order to communicate the inside of the elastic tube section 400 with the interior of the breathing tube. As a consequence of the foregoing construction, the elastic tube 400 will act as a balloon and by properly selecting the physical parameters (length, material thickness and elasticity) the elastic section will protect the patient in the same manner as an inelastic breathing bag. However, the cost of the elastic section 400 plus a plastic breathing bag is considerably less than the cost of an elastic breathing bag. Moreover, with conventional anesthesia layout, the elastic tube 400 is more likely to be located in a position at which it can be observed by the attending anesthetist.

In accordance with a further modification of the invention as shown in FIGS. 26 and 27, the elastic tube 400 of FIG. 24 can be modified to function as an overpressure relief means, thus constituting an alternative to the incorporation of the overpressure relief means with the Y-piece as shown in FIGS. 14-16. In order to incorporate an overpressure relief means within the elastic section 400, an elastic band 410 is mounted around the section 400 between the sealed ends 404 and 406 and the section 400 is slit at 412 between the band 410 and one end. Preferably, some filler material 411 is provided between corrugations beneath the band 410. As the pressure within the breathing tube 402 increases, the tube 400 will stretch and at a certain point stretch the elastic band 410 away from the breathing tube so as to permit leakage beyond the band 410. The gas leaked beyond the band 410 is then relieved through the slit 412. Preferably, as the gas is relieved through the slit 412, the material adjacent the slit acts as a reed and creates an audible alarm to advise the anesthetist of the overpressure condition.

From the foregoing, it should be appreciated that a general anesthesia rebreathing system has been disclosed herein comprised of a disposable portion and a permanent portion and configured so as to minimize the cost and complexity of the disposable portion, while including therein all of the elements likely to produce cross contamination.

What is claimed is:

1. In a general anesthesia rebreathing system including (1) patient airway communication means, (2) fresh gas supply means, (3) at least one elongated breathing tube coupling said patient airway communication means and said fresh gas supply means, and (4) overflow valve means coupled to said breathing tube for venting excess gas therefrom at a normally encountered predetermined pressure, the improvement comprising:

overpressure relief means including first and second valve surfaces for permitting gas flow therepast in response to a positive pressure differential thereacross greater than said predetermined pressure at which said overflow valve means vents excess gas from said breathing tube;

means exposing said first valve surface to the pressure within said patient airway communication means and said second valve surface to ambient pressure; and means responsive to gas flow past said overpressure relief means for producing an audible alarm.

2. A general anesthesia rebreathing system including:

means for communicating with a patient's airway;
fresh gas supply means;
at least one elongated breathing tube coupling said patient airway communication means and said fresh gas supply means;
overflow valve means coupled to said breathing tube for venting excess gas therefrom at a normally encountered predetermined pressure; and
means responsive to the pressure in said breathing tube exceeding a physiologically safe level, in excess of said predetermined pressure, for providing an audible alarm and for relieving pressure in said breathing tube.

* * * * *